United States Patent
Kim et al.

(10) Patent No.: US 12,193,770 B2
(45) Date of Patent: Jan. 14, 2025

(54) SEVEN DEGREE OF FREEDOM POSITIONING DEVICE FOR ROBOTIC SURGERY

(71) Applicants: BOARD OF REGENTS OF THE UNIVERSITY OF TEXAS SYSTEM, Austin, TX (US); ColubrisMX, Inc, Houston, TX (US)

(72) Inventors: Daniel H. Kim, Houston, TX (US); Dong Suk Shin, Houston, TX (US); Taeho Jang, Houston, TX (US); Yongman Park, Houston, TX (US); Jeihan Lee, Houston, TX (US); Kihoon Nam, Gwangmyeong (KR); Yongchul Shin, Houston, TX (US)

(73) Assignees: Board Of Regents Of The University Of Texas System, Austin, TX (US); ColubrisMX, Inc, Houston, TX (US)

( * ) Notice: Subject to any disclaimer, the term of this patent is extended or adjusted under 35 U.S.C. 154(b) by 89 days.

(21) Appl. No.: 17/766,720

(22) PCT Filed: Jan. 17, 2020

(86) PCT No.: PCT/US2020/014022
§ 371 (c)(1),
(2) Date: Apr. 5, 2022

(87) PCT Pub. No.: WO2021/071540
PCT Pub. Date: Apr. 15, 2021

(65) Prior Publication Data
US 2024/0058079 A1 Feb. 22, 2024

Related U.S. Application Data

(60) Provisional application No. 62/914,226, filed on Oct. 11, 2019.

(51) Int. Cl.
*A61B 34/30* (2016.01)
*A61B 34/00* (2016.01)
*A61B 50/13* (2016.01)

(52) U.S. Cl.
CPC .............. *A61B 34/30* (2016.02); *A61B 34/70* (2016.02); *A61B 50/13* (2016.02); *A61B 2034/302* (2016.02)

(58) Field of Classification Search
CPC ......... A61B 34/30; A61B 34/37; A61B 34/70; A61B 2034/302; A61B 50/13; A61B 90/50
See application file for complete search history.

(56) References Cited

U.S. PATENT DOCUMENTS

| | | | |
|---|---|---|---|
| 2009/0163929 A1 | 6/2009 | Yeung et al. | |
| 2009/0234369 A1* | 9/2009 | Bax ........................ | A61B 34/30 606/130 |

(Continued)

FOREIGN PATENT DOCUMENTS

| | | |
|---|---|---|
| CN | 106344160 B | 9/2019 |
| EP | 2253288 A2 | 11/2010 |

(Continued)

OTHER PUBLICATIONS

Korean Patent Application No. 10-2022-7011021, Office Action dated Jan. 16, 2024, 13 pages.

(Continued)

*Primary Examiner* — Tan-Uyen T Ho
*Assistant Examiner* — Cherie M Poland
(74) *Attorney, Agent, or Firm* — Patterson + Sheridan, LLP

(57) ABSTRACT

An instrument cart configured to position an instrument controller at a desired location and attitude pitch with respect to an incision location of a patient includes a base, (Continued)

a lift member moveable with respect to the base, a first planar translation member connected to the lift member and arcuately moveable with respect thereto, a second planar translation member connected to the first planar translation member and arcuately moveable with respect thereto, a third planar translation member connected to the second planar translation member and arcuately moveable with respect thereto, an arcuate slide base connected to the third planar translation member and moveable with respect thereto and an arcuate slide coupled to the arcuate slide base, and moveable with respect thereto; and an instrument controller coupling connected to the arcuate slide member, the instrument controller connected thereto and movable with respect thereto.

9 Claims, 15 Drawing Sheets

(56) References Cited

U.S. PATENT DOCUMENTS

| | | | | |
|---|---|---|---|---|
| 2011/0282351 | A1* | 11/2011 | Cooper | G03B 35/00 |
| | | | | 606/108 |
| 2012/0029277 | A1* | 2/2012 | Sholev | A61B 90/50 |
| | | | | 600/102 |
| 2013/0053866 | A1 | 2/2013 | Leung et al. | |
| 2018/0140377 | A1* | 5/2018 | Reichenbach | B25J 18/02 |
| 2019/0223972 | A1 | 7/2019 | Fischer et al. | |
| 2019/0269571 | A1 | 9/2019 | Park et al. | |

FOREIGN PATENT DOCUMENTS

| | | |
|---|---|---|
| JP | S6247890 A | 3/1987 |
| JP | 2009512473 A | 3/2009 |
| JP | 2012501866 A | 1/2012 |
| JP | 2013530738 A | 8/2013 |
| JP | 2019516531 A | 6/2019 |
| JP | 6562174 B1 | 8/2019 |
| KR | 10-2018-0008795 A | 1/2018 |
| WO | 2018147930 A1 | 8/2018 |

OTHER PUBLICATIONS

Canadian Patent Application No. 3,152,170, Office Action dated Jun. 13, 2023, 4 pages.
Japanese Patent Application No. 2022-518261, Office Action dated Apr. 18, 2023, 12 pages.
PCT International Application No. PCT/US2020/014022, International Search Report and Written Opinion dated Jul. 9, 2020, 17 pages.
Japanese Patent Application No. 2022-518261, Final Office Action dated Nov. 7, 2023, 10 pages.

* cited by examiner

SEVEN DEGREE OF FREEDOM POSITIONING DEVICE FOR ROBOTIC SURGERY

CROSS-REFERENCE TO RELATED APPLICATION

This application for Patent is a national stage application under 35 U.S.C. 371 of PCT/US2020/014022, filed Jan. 17, 2020, which claims benefit of U.S. Provisional Application Ser. No. 62/914,226, filed Oct. 11, 2019, which are herein incorporated by reference in their entirety.

BACKGROUND

Field

The present specification relates to robotic surgical systems and procedures used for minimally invasive surgery. More specifically, the present specification relates to the field of positioning devices useful for use in minimally invasive surgery.

Description of the Related Art

Noninvasive, or non-highly invasive, surgery techniques using tubular members to position cameras, surgical tools such as clamps, cutting elements, sutures, etc., have been developed to avoid the need to form large incisions in the skin of a patient, such as a mammal, including humans, to survey a body interior site or to perform surgery on a body interior site. In these techniques, the tip or distal end of the tubular device is guided through anatomy using a series of cables configured to selectively bend the tip of the tubular device, as well as progress or retract the tip end of the tubular device, as well as the tubular device itself, within the anatomical architecture. The physician follows the progression of the tip end within the anatomy by watching a screen on which an image or images captured by a camera on or near the distal end of the tubular device is displayed, and manipulates the orientation of the tip end of the tubular member, as well as the progression or regression thereof, to control the aforementioned wires using a control device such as a master device equipped with joysticks. The control of the wires to effectuate these movements of the tip end of the tubular device are accomplished by mechanical elements, such as a series of motors, connected to the wires in an instrument controller at a location exterior of the patient. The weight of the instrument controller is substantial, typically on the order of 700 or more Kg, and the instrument controller must be controllably supported exteriorly of, and proximal to, the patient and proximal to the entry point of the tubular device into the patient.

During surgery, the distal tip of the tubular device is inserted, through an incision, into the body anatomy. This may occur vascularly, where the tubular device is pushed up or along a blood vessel, or simply between or along interior body anatomy. If the tubular device is thus deployed, and the portion thereof immediately adjacent to the incision is laterally shifted, injury to the patient undergoing a surgical procedure can occur. The instrument controller is also typically located immediately adjacent to the incision in the patient to increase the control over the tubular deployable device, because if a portion of the tubular deployable device is present between the mechanical control elements and the incision, that portion tubular member of the tubular deployable device can bow between the instrument controller and the incision, reducing the response parallelism between the controller and the tip of the tubular member, and also potentially tearing the incision or undesirably changing the orientation of the tubular member within the patient.

SUMMARY

An instrument cart configured to position an instrument controller at a desired location and attitude pitch with respect to an incision location of a patient includes a base, a lift member moveable with respect to the base, a first planar translation member connected to the lift member and arcuately moveable with respect thereto, a second planar translation member connected to the first planar translation member and arcuately moveable with respect thereto, a third planar translation member connected to the second planar translation member and arcuately moveable with respect thereto, an arcuate slide base connected to the third planar translation member and moveable with respect thereto, an arcuate slide coupled to the arcuate slide base, and moveable with respect thereto, and an instrument controller coupling connected to the arcuate slide member, the instrument controller connected thereto and movable with respect thereto.

DETAILED DESCRIPTION

Figure 1:
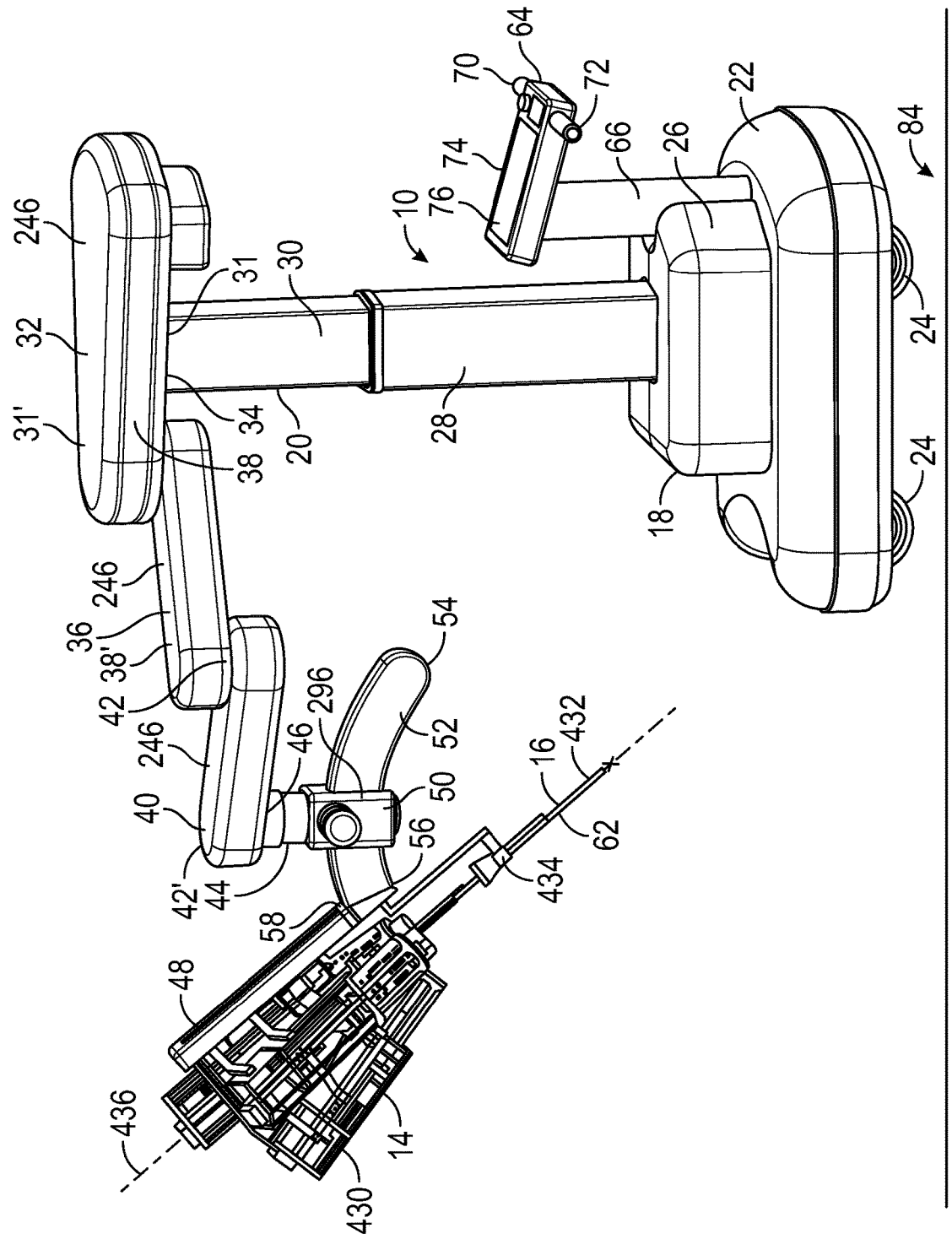
FIG. 1 is an isometric view of an instrument cart configured to controllably support a deployment apparatus, for example an instrument controller, thereon.
Figure 2:
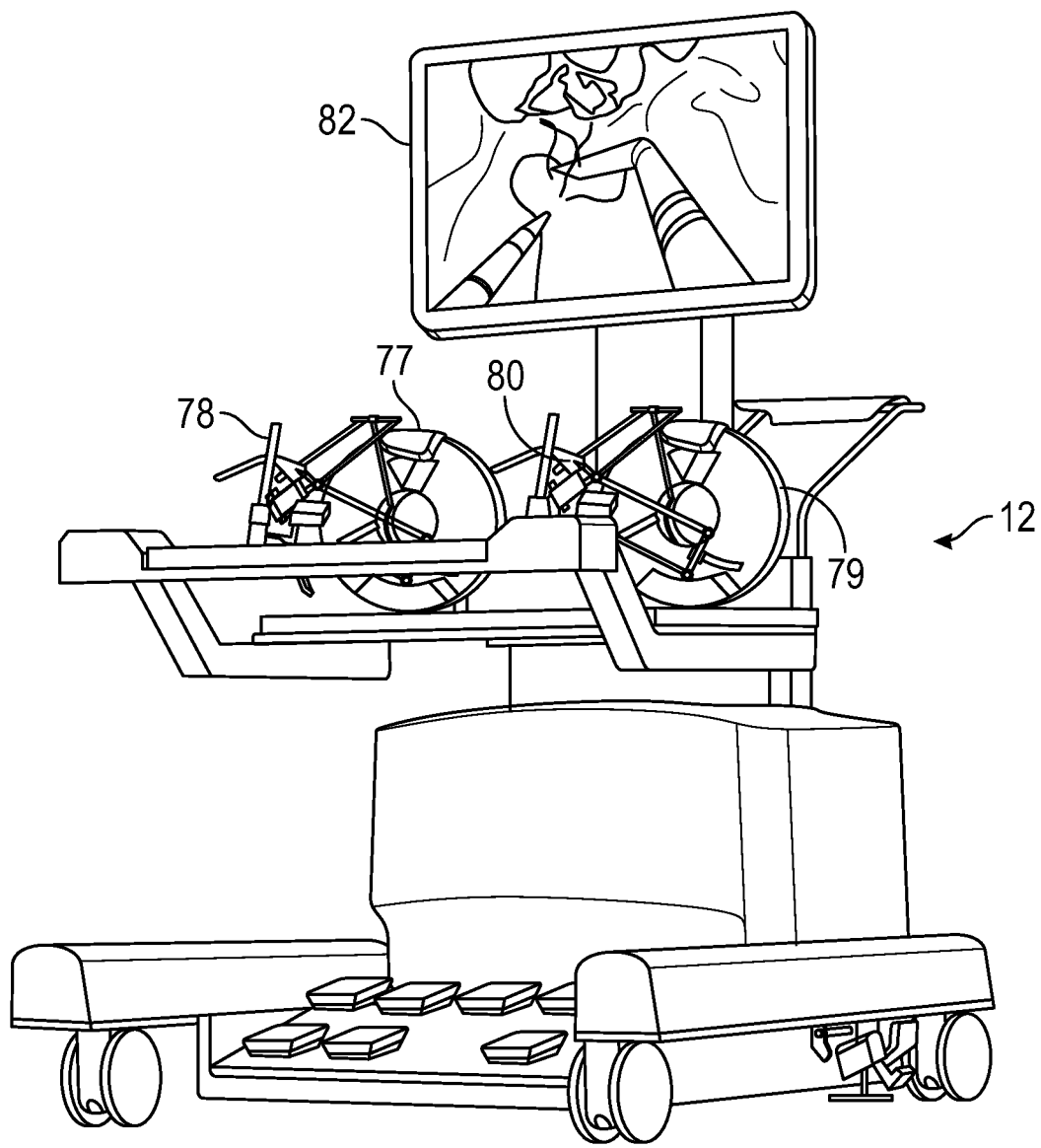
FIG. 2 is an isometric view of a control console.

Referring initially to FIGS. 1 and 2, an instrument cart 10 (FIG. 1), and a control console 12 (FIG. 2), are shown. The instrument cart 10 here is configured to allow positioning of an instrument controller 14 suspended therefrom relative to an incision location 16 (location X on FIG. 1) of a patient, such as a mammal, including humans. The instrument cart 10 generally includes a cart base 18 and a positioning portion 20, extending upwardly from the cart base 18 and supported on the cart base 18. The cart base 18 is configured to roughly position the instrument controller 14 adjacent to a patient and the incision location 16 thereof. It includes a base pedestal 22 supported over a plurality of rotatable wheels 24 (four, only two of which are shown) allowing the base pedestal to be moved along a floor 84, a drive portion 26 positioned above, and over, the base pedestal 22, and a tubular receiver 28 extending upwardly from the drive portion 26 within which an elevating tube 30 is received. To position the instrument cart 10 relative to a patient incision location 16, a user such as an operating room technician pushes the instrument cart 10 to a desired location of the instrument controller 14 with respect to a patient, and then locks the wheels in place using friction brakes or wheel locks (not shown) as known in the art. The positioning portion 20 includes the elevating tube 30 which telescopically moves within, and selectively extends from, tubular receiver 28, a first planar translation member 32 rotatably supported at the upper, distal end 34 of the elevating tube 30 at a first pivot 31 location distal to the tubular receiver 28, a second planar translation member 36 rotatably suspended from the first planar translation member 32 at second pivot 38 location, a third planar translation member 40 rotatably suspended from the second planar translation member 36 at a third pivot 42 location, distal to second pivot 38 location, a center of motion coupling 44 rotatably coupled to, and suspended from, the third planar translation member 40 at a fourth pivot 46 location distal of the third pivot 42 location, and a linear slide 48 coupled to the center of motion coupling 44, to which the instrument controller 14 is connected for relative movement therebetween.

First, second and third planar translation members 32, 36 and 40 are each arcuately coupled at a respective pivot 31, 38 and 42 location, to allow the free ends 31', 38' and 42', i.e., the end distal to their pivot or rotation location, of each of the first, second and third planar translation members 32, 36 and 40 to swing or rotate thereabout such that the end thereof distal to the pivot on which they are respectively located swings through an arc centered on the respective pivot 31, 38 and 42 location. Each of first, second and third pivot 31, 38 and 42 locations are belt and motor-driven, for controllable arcuate movement thereof about their respective pivots, and together take the form of a SCARA (Selective Compliance Assembly Robot Arm) style of robot, which enables both linear and arcuate movement of the fourth pivot 46 location with respect to the first pivot 31 location. Here, second pivot location 38 is located adjacent first free end 31', third pivot 42 location is adjacent to free end 38', and fourth pivot 46 location is adjacent to free end 42'. Center of motion coupling 44 includes a drive housing 50 which is pivotally connected and suspended from the third planar translation member 40 at the fourth pivot 46 location, and an arcuate driven slide 52 which is coupled to the drive housing 50 and linearly moveable, along the circumference of an arc thereof, with respect to the drive housing 50. Arcuate driven slide 52 includes opposed first and second ends 54, 56, and linear slide 48 extends from the arcuate driven slide 52, from a coupled location 58 at second end 56 thereof coupled to second end of the arcuate driven slide 52. Linear slide 48 includes a centerline 420 (FIG. 11), which centerline 420 is positioned perpendicular to a tangent of a circumference along which the arcuate driven slide 52 extends, and linear slide 48 extends away from the arcuate driven slide 52 in the direction away from the center 62 of the circumference of the arc along which driven arcuate member 52 extends, which, when the instrument controller is properly positioned, overlies and aligned to, or is immediately adjacent to, the incision location 16 of a patient.

Instrument cart 10 further includes a cart control unit 64 positioned over the cart base 22, and supported therefrom on a hollow cart control unit pedestal 66. A control housing 74 is mounted to the upper end of the cart control unit pedestal 66, from which a pair of drive handles 70, 72 extend from opposed sides thereof in a generally horizontal direction, and a control screen 76 configured, for example, as a touch screen to selectively select options displayed thereon, is supported on or in the control housing 74. The control screen 76 and the handles 70, 72 are positioned on the order of 2.5 to 4 feet from the floor 84.

The control console 12 of FIG. 2 is configured to enable an operator, such as a physician, surgeon or technician, to manipulate the distal tip of an insertion tube 432 of an intraluminal or other introductory device deployed by the instrument controller 14 within the body of the patient. Although not shown in the FIGS., one or more robot arms, equipped with various end-effectors (such as grippers, cameras or other tools), are mounted at the end of the distal tip of the insertion tube 432. For the manipulation purpose, the control console 12 comprises a first master device 77 and a second master device 79, each having a joystick or other hand holdable or directable element, here first and second joysticks 78, 80, respectively, associated therewith, one of each of which is held in one of the hands of the operator, and a screen 82 displaying an image captured from a camera at, or immediately adjacent to, the tip end of the insertion tube 432 (FIG. 1) of the intraluminal or other tubular introductory device extending from the instrument controller 14. Here, one master device, for example first master device 77, is used to direct forward or rearward movement of insertion tube 432 (FIG. 1) of the intraluminal or other tubular introductory device with respect to the incision location 16 using motion of the first joystick 78 thereof, and the other, for example second master device 79 is manipulatable to change the orientation of the mounted instruments (such as robot arms, end-effectors, or cameras) and tip end itself of the intraluminal or other introductory device using motion of the second joystick 80 thereof. As a result, the operator can steer the tip of the intraluminal or other introductory device, and thus the intraluminal or other introductory device itself, within the body of the patient.

Figure 3:
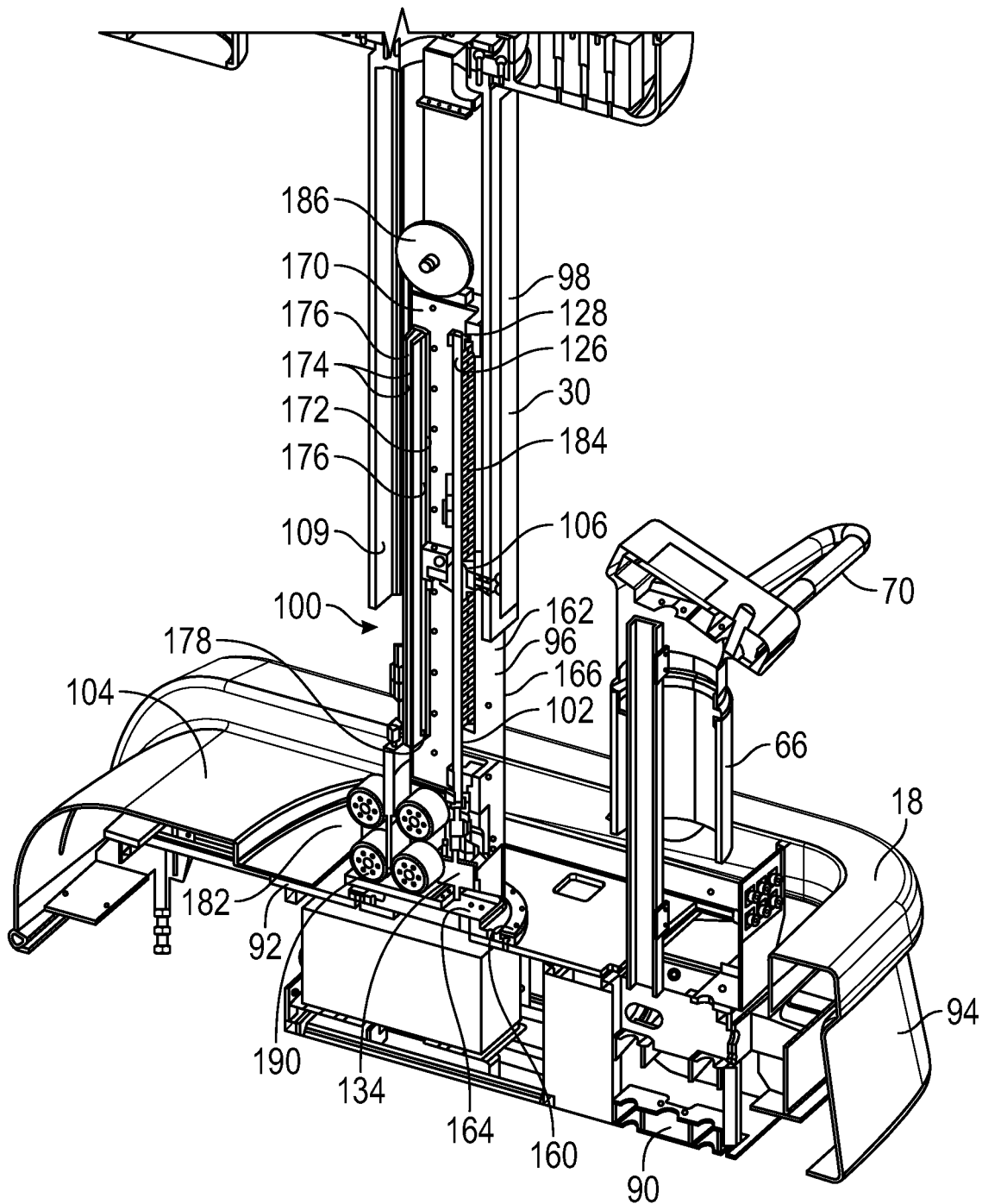
FIG. 3 is a cutaway view of the base of the instrument cart and the lift portion extending therefrom.
Figure 4:
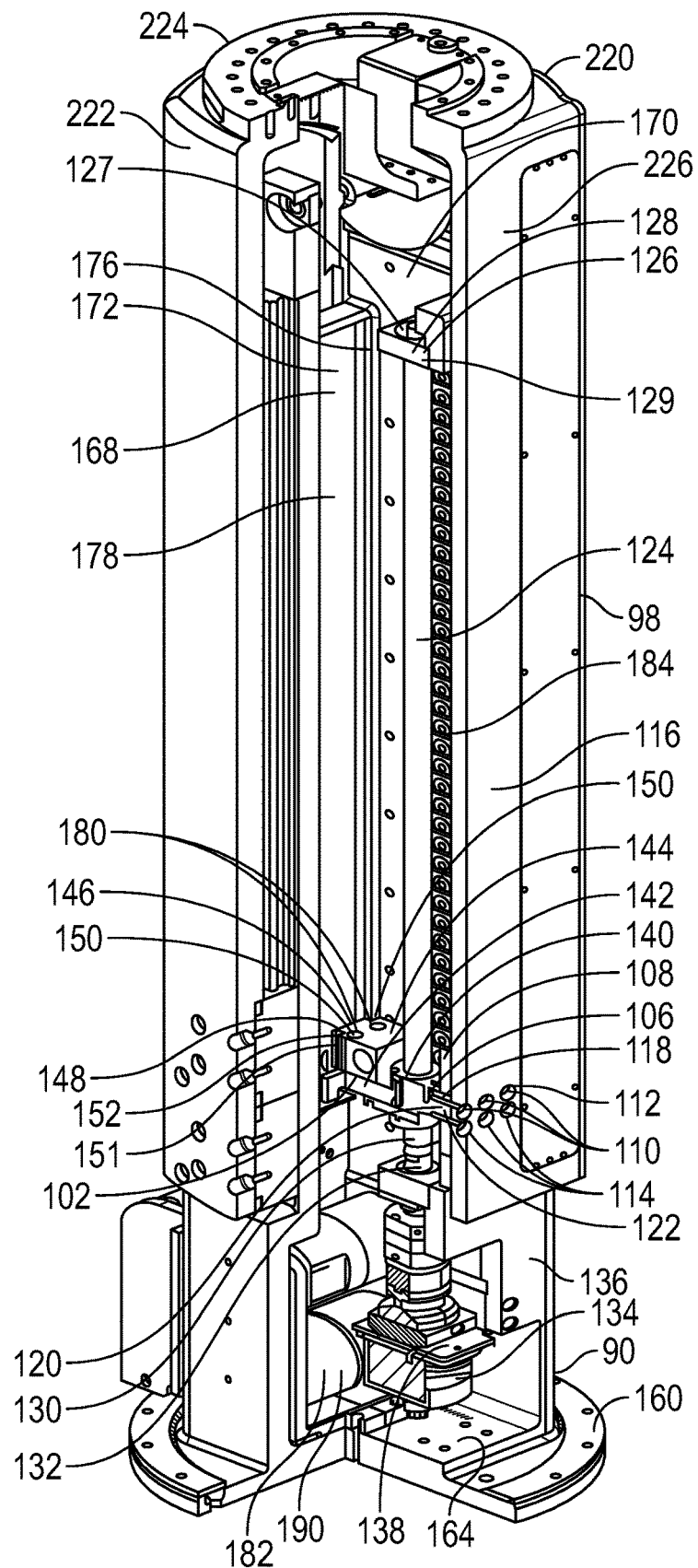
FIG. 4 is a first partial cutaway view of a stationary lower portion of the base and the lift portion.

Referring now to FIGS. 3 to 5, the interior structures of the tubular receiver 28 of the cart base 18 and the interconnection thereof to the elevating tube 30 of the positioning portion 20 which allows the elevating tube 30, one end of which is telescopically received in the tubular receiver 28, to move inwardly and outwardly of the tubular receiver 28 to position the first, second and third planar translation members 32, 36 and 40 at a desired elevation above a base reference location or plane, such as a floor 84 of an operating theater is shown. In FIGS. 3 to 5, the interior structures of the tubular receiver 28 are shown with the outer skin or shell of the tubular receiver 28 within which the elevating tube extends and retracts removed. In FIG. 3, the elevating tube 30 is shown elevated or extending upwardly from the cart base 18, and in FIGS. 4 and 5, the elevating tube 30 is shown in its lowermost, or fully retracted, position, to the full extent it can be telescoped into the outer skin or cover of the tubular receiver 28.

Cart base 18 internally generally includes a lower base portion 90 and an upper base portion 92 supported over the lower base portion 90, surrounded by a shroud 94 providing a skin or cover over the operating elements of the cart base 18. The tubular receiver 28 includes a stationary lower portion 96 extending upwardly from the upper base portion 92. The elevating tube 30 generally includes a lift portion 98 slidingly received over the stationary lower portion 96. A lifting drive 100 configured to move the lift portion 98 upwardly and downwardly over, and with respect to, the stationary lower portion 96 extends between, and forms a portion of each of, the lift portion 98 and the stationary lower portion 96 and is configured to selectively position the lift portion 98 in the vertical direction relative to the stationary portion 96 of the tubular receiver 28. Here, lifting drive 100 includes a positive positioning drive 102 and a gravity compensation system 104 configured to counterbalance the weight or mass of the elevating tube 30, the positioning components thereon, and the instrument controller 14 to reduce the power or energy required to be supplied to a motor to lift these elements.

Figure 6A:
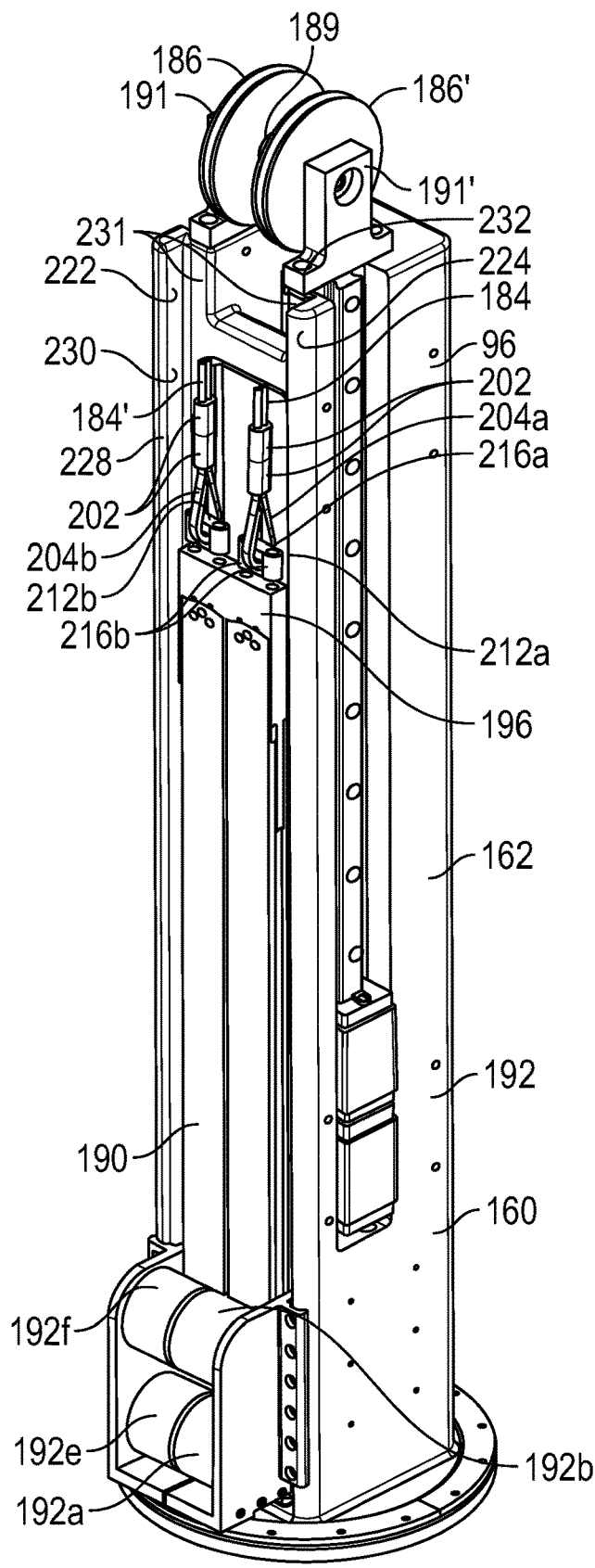
FIG. 6A is an isometric view of a stationary lower portion and base of FIGS. 5A and 5B, with the lift portion removed, showing the position of certain components of a gravity compensation system when the lift portion is in a fully retracted or fully lowered, position.
Figure 6B:
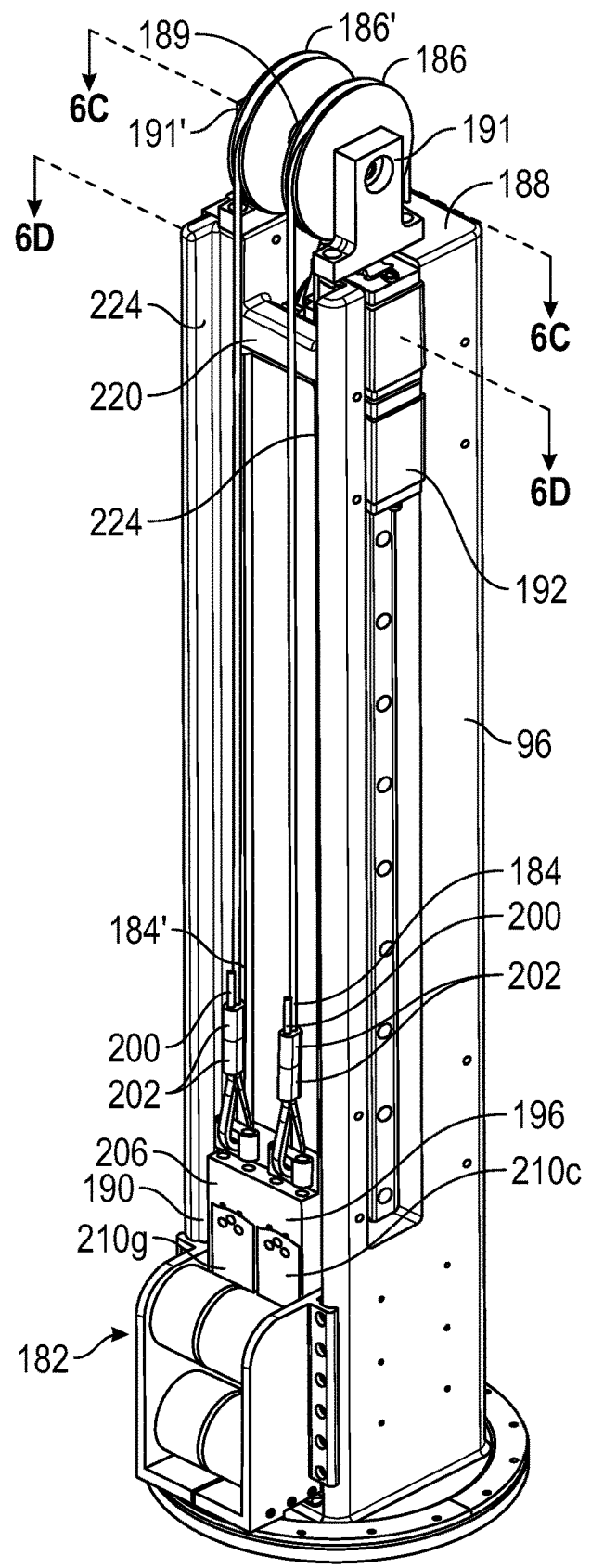
FIG. 6B is an isometric view of a stationary lower portion and base of FIGS. 5A and 5B, with the lift portion removed, showing the position of certain components of a gravity compensation system when the lift portion is in a fully extended or fully raised position.
Figure 6C:
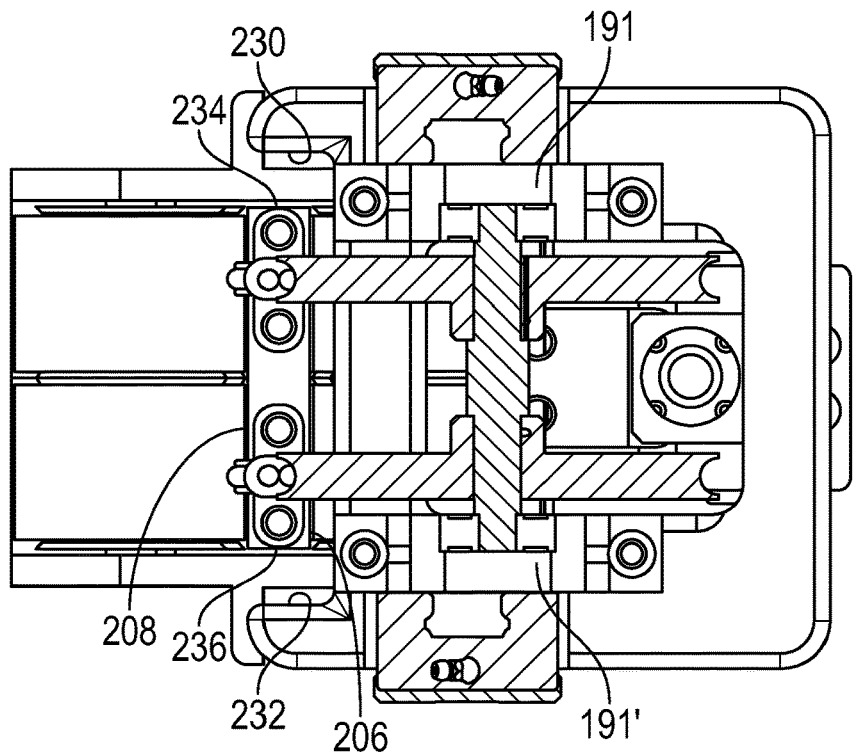
FIG. 6C is a sectional view of the stationary lower portion and base of FIG. 6A at section 6C-6C.
Figure 6D:
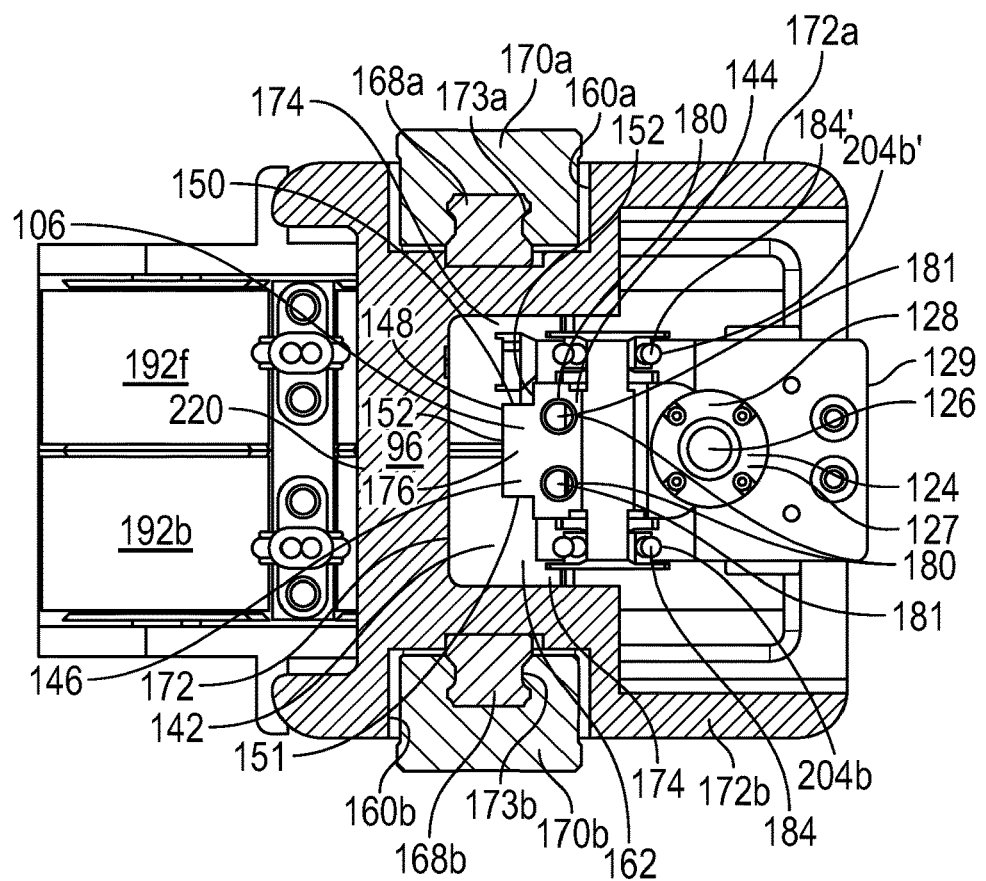
FIG. 6D is a sectional view of the stationary lower portion and base of FIG. 6B at section 6D-6D.

Referring to FIGS. 4 and 6D, the positive positioning device 102 is here configured as a lead screw system, wherein a non-rotating threaded aperture plate 106 having a threaded aperture 140 extending therethrough is secured to the lift portion 98 within the interior 108 thereof by a plurality of securing members, here a plurality of threaded fasteners 110, the heads 112 of which are received in countersunk apertures 114 extending inwardly of the exterior wall of the shroud forming the structural body 116 of the lift portion 98, and the shanks 118 thereof extend from the heads 112 into threaded holes 120 extending inwardly of a standoff 122 which supports the threaded aperture plate 106 at a fixed vertical location relative to the interior of the structural body 116. A threaded rod 124, having a first end 126 supported in a bearing assembly 128, and a second, driven second end 130 connected, through a gearhead or coupling 132, to a drive motor 134, is received within and extends through the threaded aperture 140. Drive motor 134 is rigidly connected to lower base portion 90 by a motor support bracket 136 through an L-shaped bracket 138 connected therebetween. Thus, drive motor 134 is supported in the vertical and horizontal directions against movement, but the threaded rod 124 is rotatable about its own axis by rotation of the motor 134. Bearing assembly 128 includes a bearing 127 received over the first end 126 of the threaded rod 124, the bearing 127 received in a bearing support block 129 connected to the interior of the exterior structural body 116 to support the first end 126 of the threaded rod 124 against lateral or linear movement with respect to the structural body 116 of the lift portion 98 and to maintain the longitudinal centerline of the threaded rod 126 in a generally vertically extending direction.

To further prevent relative rotation between the lift portion 98 and the stationary lower portion 96 in the horizontal plane, the threaded aperture plate 106 includes a stabilizing bracket 142 portion extending therefrom in the direction away from the portion thereof connected to the interior wall of the exterior structural body 116 by the threaded fasteners 110, on which a spline block 144 is secured, such as by threaded fasteners (not shown) and corresponding apertures and threaded apertures (not shown) in the spline block 144 and the stabilizing bracket 142. Spline block 144 includes, on the side 152 thereof opposed to the threaded aperture thereof, an extending spline 146, which is a generally rectangular projection projecting from the side 152 of the spline block 144, and which includes opposed flat sides 150, 151 extending outwardly of the side 152 in the horizontal direction and extending vertically along from the side 152, and interconnected distal to the side along a spline face 148, together forming the spline 146 extending outwardly as an integral portion of the spline block 144. Spline block 144 and apertures plate 106 on which it is mounted further include a pair of spaced apertures 180 extending therethrough in the generally vertical direction, parallel to the threaded rod 124, each of which receive a landing rod 181 (FIG. 6D) extending therethrough in a direction parallel to the threaded rod 124. Landing rods 181 include, at their lowermost ends, an enlarged circumference portion (not shown) larger in circumference than that of the apertures 180, such that movement of the spline block toward the cart base 18 is limited by the engagement of the underside of the aperture plate 106 with an enlarged circumference portion of the landing rods 181 when aperture plate 106 is moving in the cart base 106.

Rotation of the threaded rod 124 by the motor 134 in a first rotational direction causes the threaded aperture plate 106, and the structural body 116 connected thereto, to move in a first linear direction relative to the lower base portion 90, for example upwardly with respect to the lower base portion 90 and the floor 84, and reverse rotation of the motor 134 causes reverse rotation of the threaded rod 124, to cause the aperture plate 106 and the structural body 116 connected thereto to move in the opposite linear direction, for example downwardly toward the lower base portion 90 and the floor 84.

As best shown in FIG. 3, stationary lower portion 96 includes a mounting portion 160 connecting the stationary lower portion 96 to the upper base portion 92, and a support body 162 portion having a lower mounting flat 164 and a support portion 166 extending generally perpendicular thereto and in the vertical direction upwardly therefrom. Motor 134 is connected to support body 162 adjacent to the mounting portion 160, wherein the support portion 166 extends vertically from the lower mounting flat. A spline guide recess 176 extends inwardly of the threaded aperture plate facing side of the support portion 166, and received therein are a pair of recess plates 174, together forming a spline guide recess 176 into which the spine 146 of the spline block 144 extends. The width of the gap between the opposed facing walls of the spline guide recess 176 in the horizontal direction is slightly larger, on the order of 0.71 of an inch greater than, the distance, in the horizontal direction, between the opposed flat sides 150, 152 of the spline block 144. As a result of the relative sizes of the width of the gap between the opposed facing walls of the spline guide recess 176 in the horizontal direction and, the distance, in the horizontal direction, between the opposed flat sides 150, 152 of the spline block 144, the spline 146, fits into and is moveable in the vertical direction within, the spline guide slot 176 without binding.

Figure 5A:
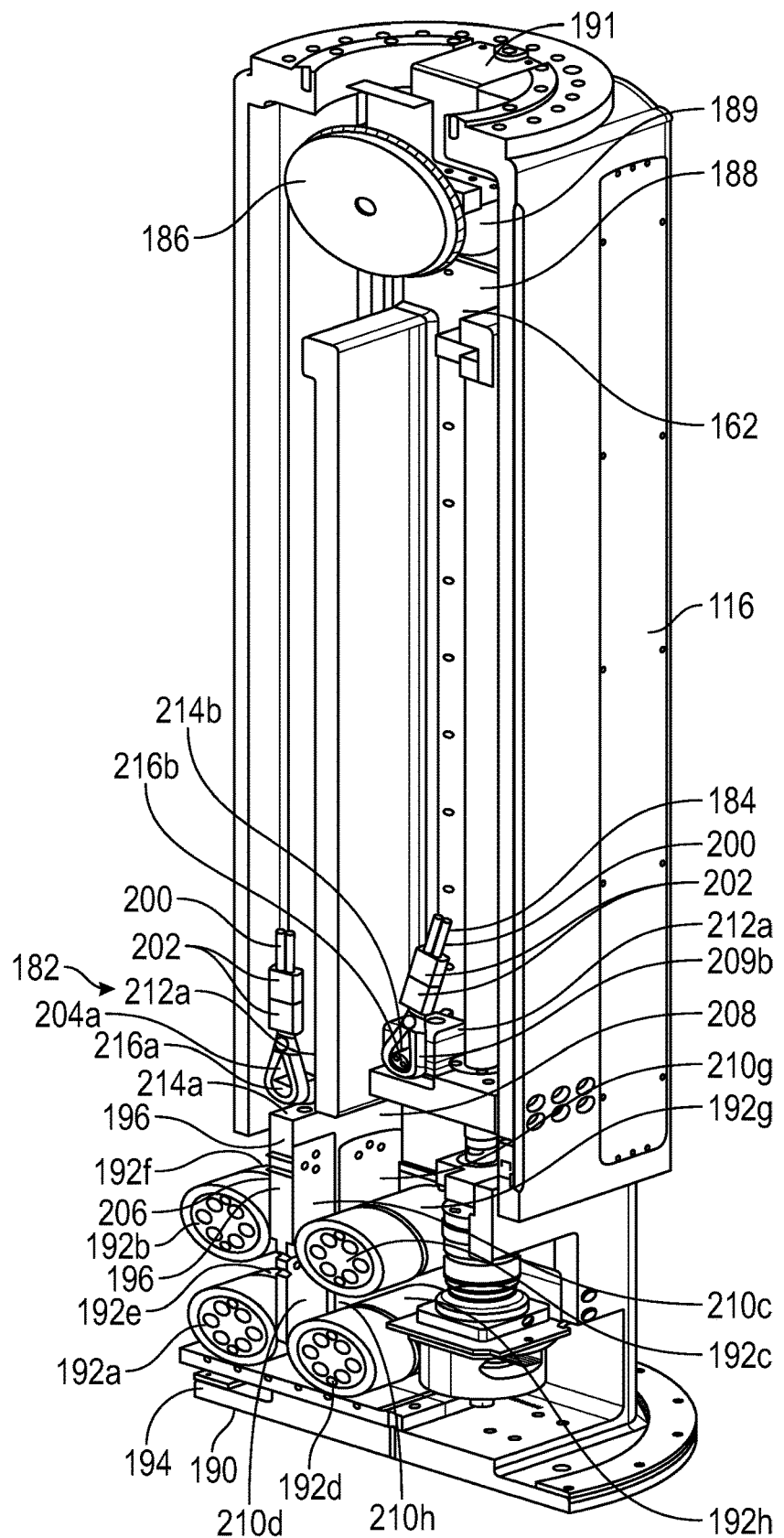
FIG. 5A is a second partial cutaway view of a stationary lower portion of the base and the lift portion.
Figure 5B:
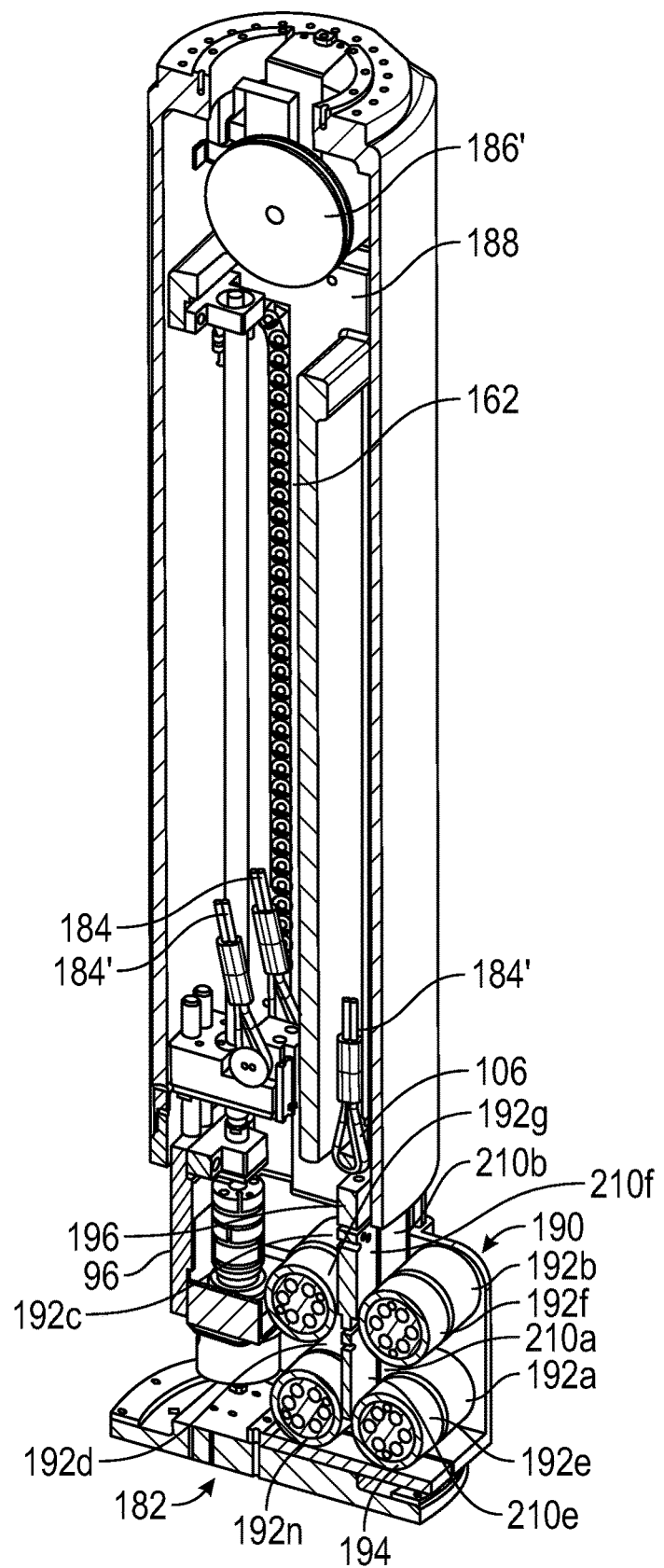
FIG. 5B is a reverse partial sectional view of the stationary lower portion of the base and the lift portion of FIG. 5.

Referring to FIGS. 6A and 6D, on opposed exterior walls 172a, 172b of the support portion 166, a pair of opposed, structural body guide recesses 160a,b extend inwardly thereof, wherein the spline guide slot 176 is disposed within the support portion and located between the opposed structural body guide recesses 160a,b. A contoured guide spline 168a, 168b is located at the base of each of the structural body guide recesses 160a, b and generally centered in the width direction of each of their respective structural body guide recesses 160a, b. Each of the structural body guide recesses 168a, b and the contoured guide spline 168a, 168b extend from the lowest elevation location of the threaded aperture plate 106 therein to the uppermost surfaces thereof. A pair of structural body guide blocks 170a, 170b, secured to opposed inner sides of the structural body 116, include mating contoured slots 173a, b matching the contour of the guide splines 168a, b, are received over the guide splines 168a, b. The guide splines limit cocking or rotational movement of the structural body 116 with respect to the support portion 166, and, together with the extending spline 146 of the aperture plate 106, limit rotational motion of the aperture plate about the threaded rod 124. The threaded aperture plate 106 is supported in a cantilevered fashion on the threaded rod 124, and when the threaded rod 124 rotates, it causes the aperture plate 106 to move vertically thereon Absent a gravity compensating system, the entire weight or mass of the lift portion 98 and the components connected thereto, on the order of 700 or more kilograms, would be supported at the contact locations of the lower flank of the threads of the threaded opening 140 with the portion of the upper flank of the threads of the threaded rod 124 currently extending through the threaded aperture 140. This leads to several issues, among which are high wear on the lower flank of the threads of the threaded opening 140 and upper flank of the threaded rod 124, uneven wear on the lower flank of the threads of the threaded aperture 140 compared to that of the upper flank of the threaded rod 124, and the need for a high torque or high horsepower motor to supply a high energy to rotate the threaded rod 124 to overcome both the static and dynamic friction between the upper flank of the threads of the threaded aperture 140 and lower flank of the threaded rod 124. Here, a gravity compensation system 182, as illustrated in FIGS. 3 to 5C, is provided to reduce the downward force of the lower flank of the threads of the threaded aperture 140 on the upper flank of the threads of the threaded rod 124. The gravity compensation system 182 operates by supplying an upwardly directed force of a magnitude approximately equal to the (gravitational) downwardly directed force of the mass of the lift portion 98 and the components connected thereto to the aperture plate 106, thereby effectively balancing the gravity based force of the lift portion 98 and the components connected thereto pressing the aperture plate downwardly with a nearly equal in magnitude, and opposite in direction, upwardly directed force.

In FIG. 3, the gravity compensation system 182 is shown along with, and connected to, cart base 18, and in FIGS. 5A and 5B, portions of the structural body 116 are shown removed to better view the interior connections of the gravity compensation system 182 and the cart base 18 is not shown. In this aspect of the gravity compensation system 182, a pair of cables, here cables 184, 184' as shown in FIGS. 5A and 5B, extend from connections thereof with the aperture plate 106 (only one shown), over freely rotatable pulleys 186, 186' (FIGS. 6A, 6B), one of each of which is dedicated to one of the corresponding cables 184, 184') connected to the opposite sides of a cross piece pulley shaft 189 supported in free rotation on the upper end 188 of the upright bracket 162 of the stationary lower portion 96 in opposed bearings in opposed pillow blocks 191, 191' secured to the uppermost end of the structural body (FIG. 6A). The cables 184, 184', after passing over the respective pulleys 186, 186', are connected, in a spaced apart fashion by approximately the distance between the location of the cables 184, 184' on the pulleys 186, 186', to the force compensation assembly 190. Each of cables 184, 184' is connected to the aperture plate 106 on opposed sides thereof and at opposite sides of spline guide recess 176 over a pin, and in a spaced apart by approximately the distance between the location of the cables 184, 184' on the pulleys 186, 186'. Here, as shown in FIGS. 5A, B and 6A-D, the gravity compensation assembly 190 includes a plurality of, here eight, coil springs 192a-h (FIG. 6), each of which is a includes a two dimensional spiral wound, strap like, spring element the inner end of which is grounded against rotation, and the opposed end 210a-h of each which is connected to a compensator strap 196.

Each of the cables 184, 184' here include a pair of opposed coupling portions 200, and a plurality of crimps 202 clamped over a portion of each of the coupling portions 200 adjacent the opposed cable ends to form loops 204a, b, but may be configured in any fashion capable of providing a continuous interconnect between the opposed loops 204a or 204b without undesirable slack therein or elongation thereof. Coupling portion 200 include a portion of the cables 184, 184' adjacent to their ends which is folded back over an adjacent part of the cable 184, 184' to form loops 204a, b, which is secured in place by the crimps 202. Here two separate crimps 202 are used to secure each opposed end of the cables 184, 184' to form the loops 204a, b, but any number of crimp elements capable of ensuring that the free ends of the cables 184, 184' remain fixed with respect to the remainder of the cable without slippage may be employed.

Compensation strap 196 includes opposed first and second spring connection faces 206, 208, wherein the portion of each of the spring elements 192a, b, e and f adjacent their ends 210 a, b, e and f respectively, is rigidly connected to the first spring connection face 206 of the compensation strap 196, and the portion of spring elements 192c, d, g and h adjacent their ends 210c, d, g and h respectively, is rigidly connected to the second spring connection face 208 of the compensation strap 196. The compensation strap 196 further includes a first strap connector 212a, having a pin 216a supported from the upper surface thereof by opposed stanchions 214a extending from the upper surface thereof. A second strap connector 212b, likewise includes a pin 216a supported from the upper surface of the spline block 144 by opposed stanchions 214a extending from the upper surface thereof. Loop 204a extends around the surface of the pin 216a, and loop 204b extends about the circumference of pin 216b. Loop 204a extends around the surface of the pin 216a, and loop 204b extends about the circumference of pin 216b, and thereby physically connects the spring elements 192a-g to the aperture plate 106 via the spline block 144 connected thereto.

As shown in FIGS. 6A and 6B, the stationary lower portion 96 includes a central rib 220 extending across and connecting the opposed walls into which the structural body guide recesses 160a, b extend, and on the side thereof opposed to the locations of the aperture plate 106 a pair of opposed flanges 222, 224 extending therefrom on opposed ends thereof, and the inner facing surfaces 230, 232 thereof together with a base 231 extending inwardly from the base of each of the facing surface 230, 232 forming a guide recess 228 in which the compensation strap 196b reciprocates. The compensation strap 196 further includes opposed side walls 234, 236 as shown in FIG. 6C extending between the opposed first and second spring connection faces 206, 208, thereof. The distance between the opposed side walls 234, 236 is less than that between the inner facing surfaces 230, 232 of the stationary lower portion 96, and thus the compensation strap 196 can move upwardly and downwardly within the guide recess 228 without physical interference with other elements of the structure.

Referring to FIGS. 6A and 6B, the position of the compensation strap 196 when the aperture plate 106 and thus the lift portion 98, is in its fully lowered position (FIG. 6A), and in its fully upwardly extended position (FIG. 6B), are shown. In each case, the downward force on the compensation strap 196 supplied by the coil springs 192a-h connected thereto at their respective end portions 210a-h provides an equal, or nearly equal, and opposite force, through the cables 184, 184', to the aperture plate 106, to counterbalance the (gravitational) force of the lift portion and the positioning elements and instrument controller 14 connected thereto downwardly on the threads of the aperture plate 106 connected thereto. In other words, as the cables 184, 184' extend between the compensation strap 196 and the aperture plate 106, the compensation system creates a spring force tending to pull compensation strap 196 downwardly toward the lower base portion 90, which force in turn is transferred, via the cables 184, 184' extending over the pulleys 186, 186', to create an upwardly biasing force on the aperture plate 106. The coil springs 192a-h are configured to provide a fairly constant spring constant over the length of the portion of each of the coil springs 192a-h extending above the horizontal location of the centers thereof. As a result, despite reeling out a portion of the coil of the coil springs 192a-h (the ends 210a-h thereof) from the coil portion thereof as the aperture plate 106 is lowered by rotation of the threaded rod 124, and reeling the portion of the spring element 194 back into the coil thereof as the aperture plate rises away from the upper base portion 92 by reverse rotation of the threaded rod 124, the upwardly directed force on the cables 184, 184' at the loops 204b, 204b' connected to the aperture plate 108 counterbalances the force of gravity on the mass (weight of the lift portion 98 and the elements supported thereon), effectively causing the lift portion 98 and the elements supported thereon to float, or appear to have a small or no mass at the interfacial contact of the lower flank of the threads of the threaded aperture 140 with the portion of the upper flank of the threaded rod 124 currently extending through the threaded aperture 140. This in turn significantly reduces the size of the motor 134 required to lift and lower the lift portion 98 and the elements supported thereon, and reduces wear on the flanks of the threaded aperture 140 and the threads of the threaded rod 124.

Figure 7A:
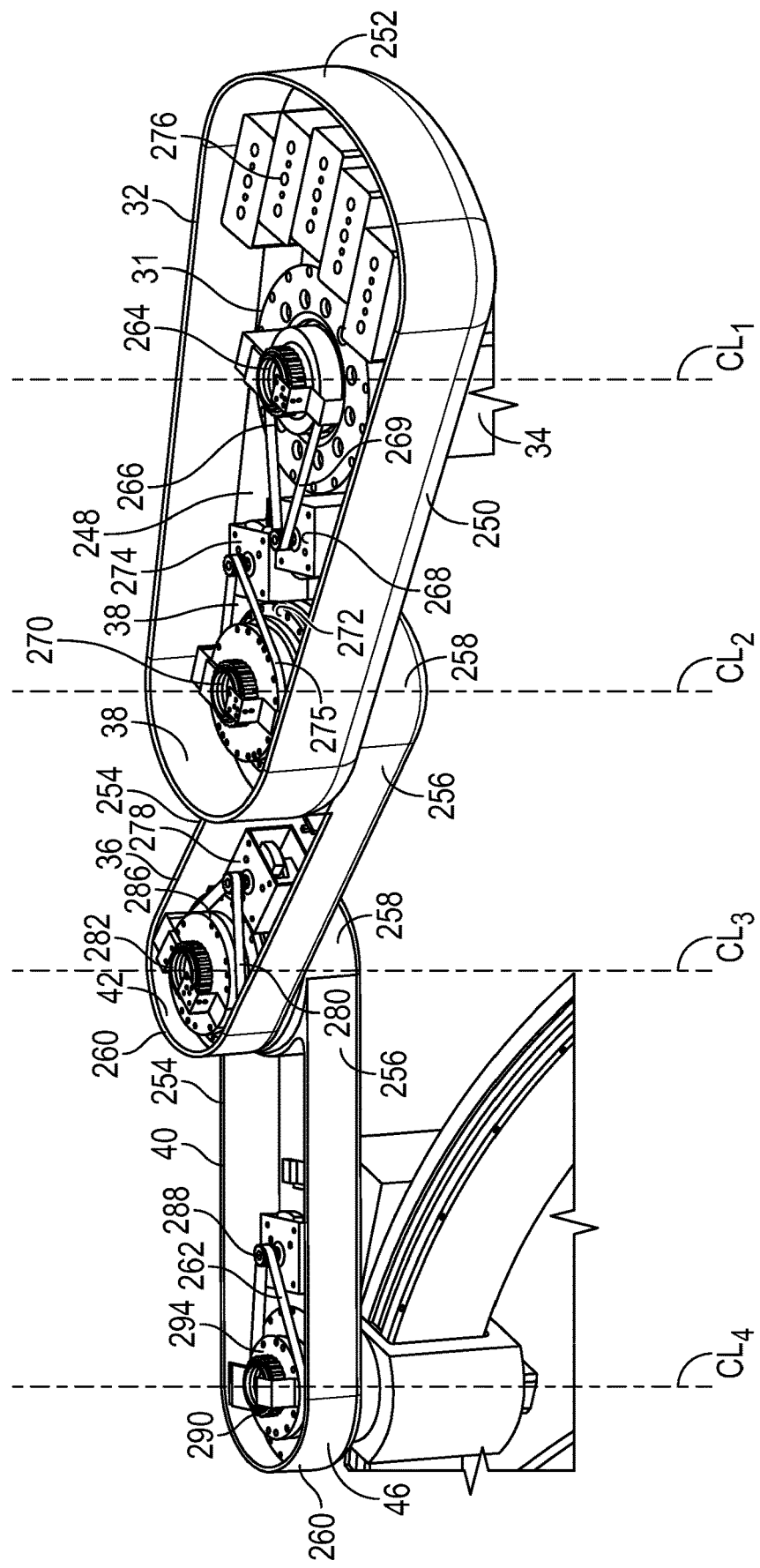
FIG. 7A is an isometric view of the three planar translation members used to laterally position an instrument controller with respect to the base.
Figure 7B:
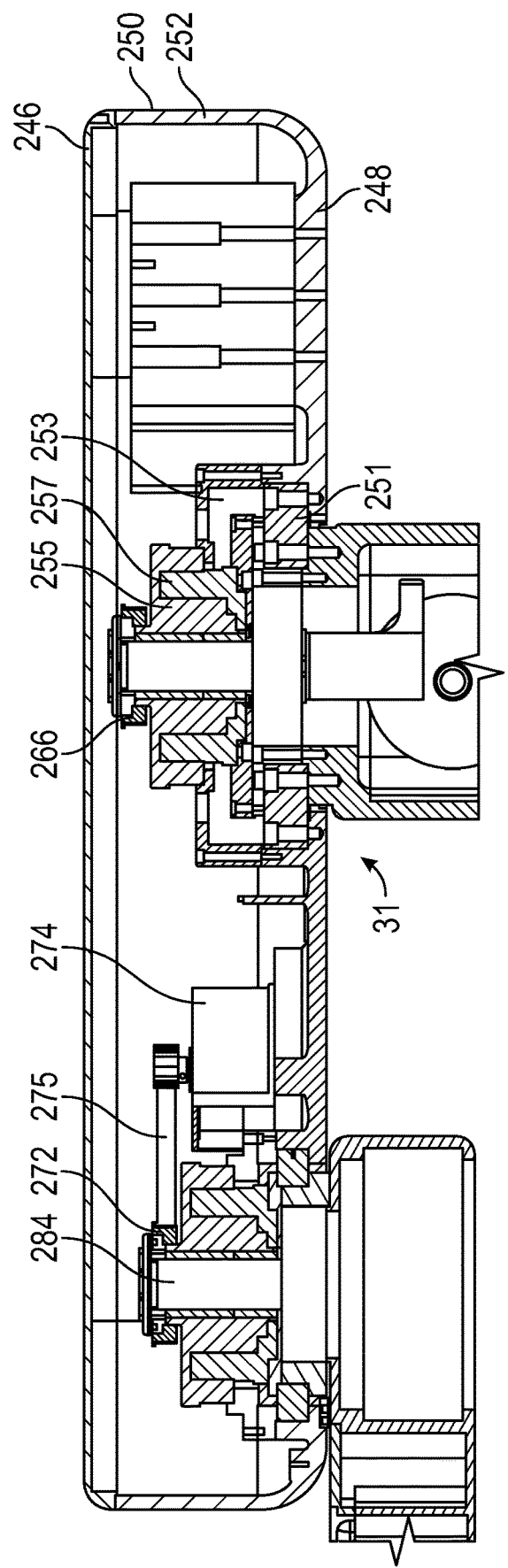
FIG. 7B is a sectional view of the first of the planar translation members of FIG. 7A.
Figure 8:
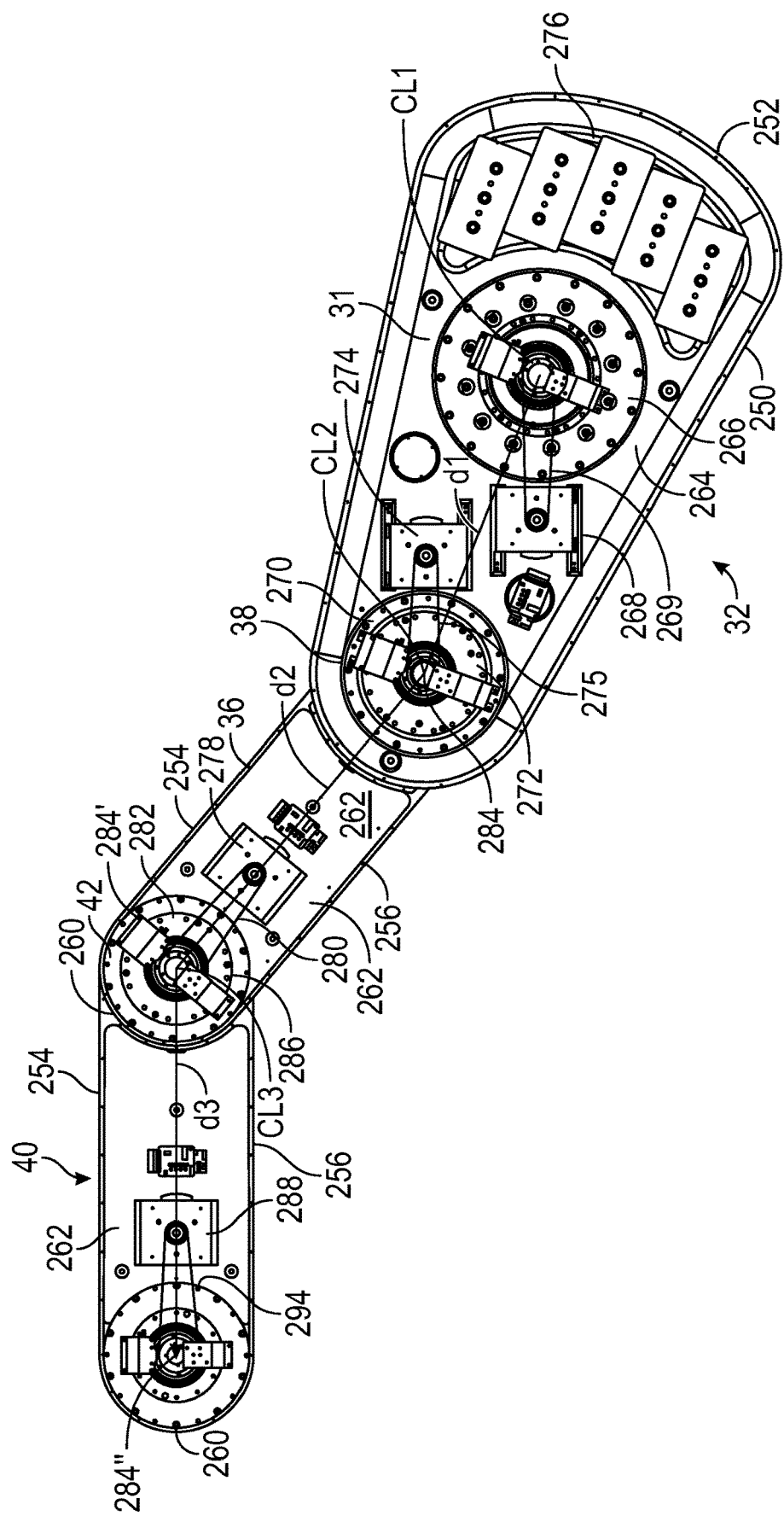
FIG. 8 is a plan view of the three planar translation members used to laterally position an instrument controller with respect to the base.

FIGS. 7A, 7B and 8 illustrate the first planar translation member 32 rotatably supported at and over the distal end 34 of the elevating tube 30 at first pivot 31 location about axis $CL_1$, distal to the tubular receiver 28, the second planar translation member 36 rotatably suspended from the first planar translation member 32 at the second pivot 38 location about axis $CL_2$ thereof, a third planar translation member 40 rotatably suspended from the second planar translation member 36 at the third pivot 42 location about axis $CL_3$, distal to second pivot 38 location, with the covers 246 (FIGS. 1 and 7B) thereof removed. Here, the first planar translation member 32 has, in plan?? view, a pie-shaped polyhedron shape or profile having a continuous circumferential edge 250, and a side wall 252 extending upwardly therefrom (away from the cart base 22 direction) and forming the edge of a pie-shaped polyhedron shape or profile, the side wall 252 and base 248 together forming a pie shaped trough. Each of second planar translation member 36 and third planar translation member 40 have opposed, generally flat and parallel to one another, first and second trough walls 254, 256 connected to each other at their adjacent ends in an arcuate first and second end walls 258, 260. First and second trough walls 254, 256 and arcuate first and second end walls 258, 260 are formed as a single continuous member. The base 262 of each of the second planar translation member 36 and third planar translation member 40 has a following edge or perimeter profile, and together with the first and second trough walls 254, 256 and arcuate first and second end walls 258, 260 forming a trough.

As shown in FIG. 7B, the motion of each of the planar translations members hereof, for example that of first planar translation member 32 about the axis $CL_1$ generally extending through the center of lift portion 98 in the vertical direction, i.e., at the pivot 31 location thereof, is affected through the operation of a harmonic drive. Each planar translation member is connected to an additional component about which it rotates through a roller or ball bearing, for example a tapered roller bearing capable of supporting the weight thereon in the vertical direction. Thus, as shown in FIG. 7A, an inner race of a roller bearing 251 is connected, through appropriate fasteners, to the upper end of the upright bracket 162, and the outer race thereof is connected, through appropriate fasteners, to the upper surface of the base 248. As a result, absent other components, first planar translation member 32 is free to rotate about the upper surface of the base 248. A coupling bracket 253 is connected to the outer race of the bearing 251 on the side thereof opposed to the base 248. A first harmonic drive 264 is connected between a shaft extending from the upper surface of the lift portion 98 and through the upper surface of the base 248 and a first pulley 266 centered on axis $CL_1$. The first harmonic drive 264 includes an input portion 255 coupled to the first pulley 266, and an output portion 257 connected to the outer race of the bearing 251.

Referring to FIG. 7A, a first motor 268 is secured to the base 248 of the first planar translation member 32, and a first belt 269 is connected over a pulley on the output shaft of the motor 268 and likewise over the first pulley 266. A second harmonic drive 270 having the same construct as the first harmonic drive 264 is connected between a second pulley 272 and a first drive shaft (284), connected to the second harmonic drive 270 through a bearing similarly to that of the connection of the first harmonic drive to the upper end of the support body 162, extending through the base 248 of the first planar translation member 32. A second motor 274 is fixed to the base 248, and a belt 275 is connected over a pulley on the output shaft of the second motor 274 and likewise over the second pulley 272. The first pivot 31 location is formed at the centerline CL1 or axis of the first harmonic drive 264. To cause the first planar translation member 32 to swing about the centerline or axis CL1 of the first pulley 266, first motor 268 rotates to cause first belt 268 to move. As the first pulley 266 is connected, through the first harmonic drive 264 to the outer race of the roller bearing 251 connected to the base 248 of the first planar translation member 32, rotation of the first pulley 266 caused by movement of the belt 269 thereon, causes the first planar translation member 32 to swing about the centerline or axis CL1. The second pivot 38 location is formed about the centerline or axis CL2 of the first drive shaft 284, whereby rotation of the second pulley 272 by the belt 275 moved by the second motor 274 causes the second planar translation member 36 to swing about with respect to the centerline or axis CL2 of the first drive shaft 284. Further, counterweights 276 are located on the base 248 at a location between the first pulley 266 and the adjacent curved portion of the sidewall 252, such that the second pulley 272 and the shaft attached thereto are on the direct opposite side of the second pulley 272 from the location of the counterweights 276.

A third motor 278 is supported on and connected to the base 262 of the second planar translation member 36, and a third belt 280 is connected over a pulley on the output shaft of the third motor 278 and likewise over a third pulley 282. The third pulley 282 is connected to a second drive shaft 284' extending therefrom and downwardly through the base 262 of the second planar translation member 36 through a third harmonic drive 286, and the second drive shaft 284' terminates rigidly connected to the base 262 of the third planar translation member 40. The third pivot 42 location is formed at the centerline or axis CL3 of the second drive shaft 284', whereby rotation of the third pulley 282 by the movement of the third motor 278 to move the third belt causes the third planar translation member 40 to swing about with respect to the centerline CL3 of the second drive shaft 284'.

Third planar translation member 40 has the same general construct as the second planar translation member 36, and includes a fourth motor 288 is supported on and connected to the base 262 of the third planar translation member 40, and a fourth belt 292 is connected over a pulley on the output shaft of the third motor 278 and likewise over a fourth pulley 290. The fourth pulley 290 is connected to a third drive shaft 284" centered to rotate about centerline or axis CL4 extending therefrom and downwardly through the base 262 of the third planar translation member 40 connected together through a fourth harmonic drive 294.

A first distance d1 extends between the centers of first and second harmonic drives 264, 270, a second distance d2 extends between the centers of the second and third harmonic drives 270, 286, and a third distance d3 extends between the centers of the third and fourth harmonic drives 286, 294. Thus, the maximum distance that the center of the fourth harmonic drive 294, and the thus the third drive shaft 284" extending therefrom, can be located from the center of the first harmonic drive 264 and thus the center of the lift portion 98 is the sum of d1+d2+d3. Thus, the centerline or axis CL4 of the third drive shaft 284", can be positioned anywhere within a circle extending around the centerline or axis $CL_1$ corresponding to the center of rotation of the first harmonic drive 264, the circle having a radius of d1+d2+d3, with a minimum span of the third drive shaft 284" from the centerline or axis $CL_1$ corresponding to the center of rotation of the first harmonic drive 264 limited by the physical size of the lift portion and the space from the center of the third drive shaft 284" to the adjacent outer wall surface of the third planar translation member 40.

Figure 9:
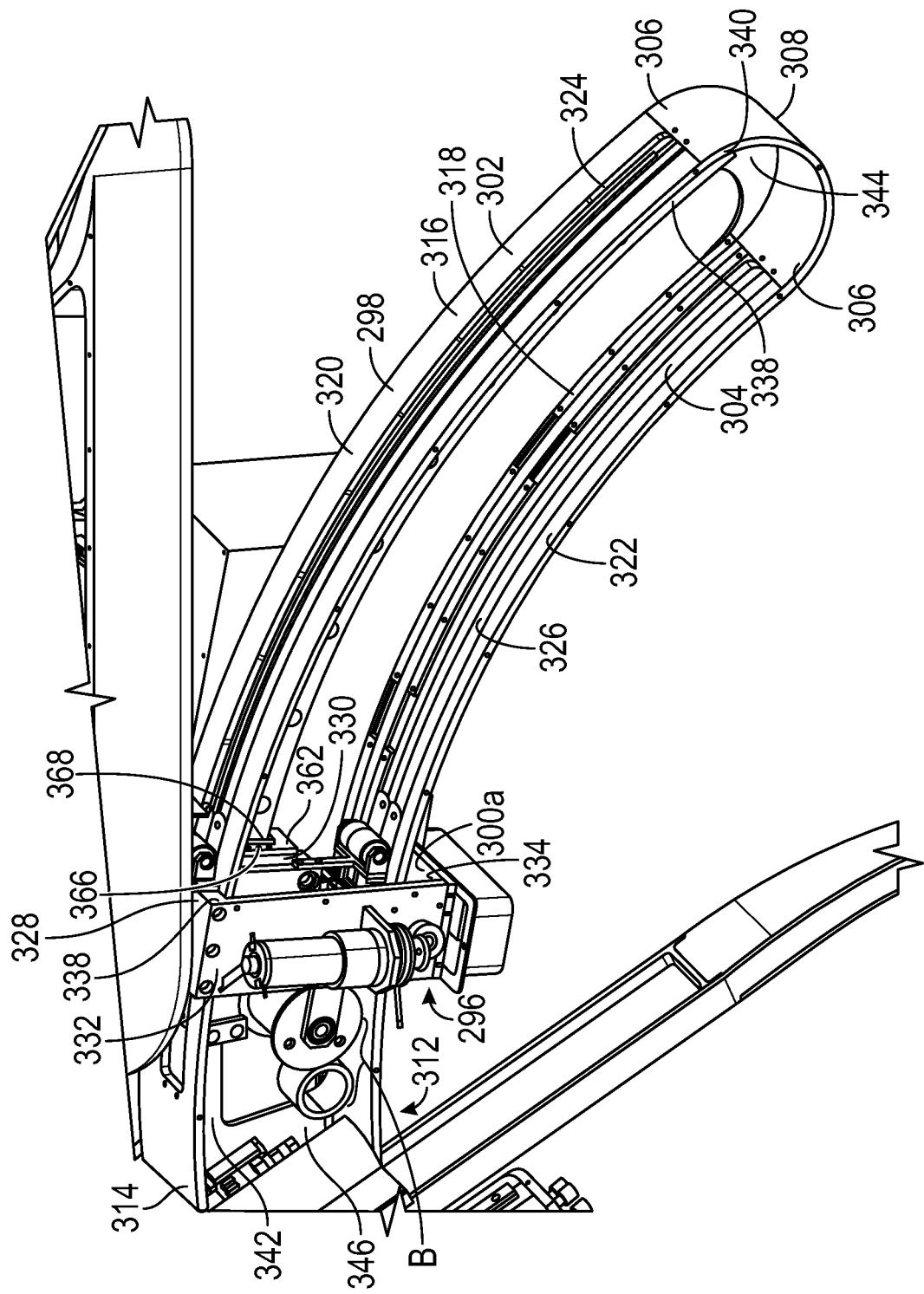
FIG. 9 is an isometric view of the interior of an arcuate slide configured to adjust the attitude, yaw or pitch of the instrument controller.
Figure 10:
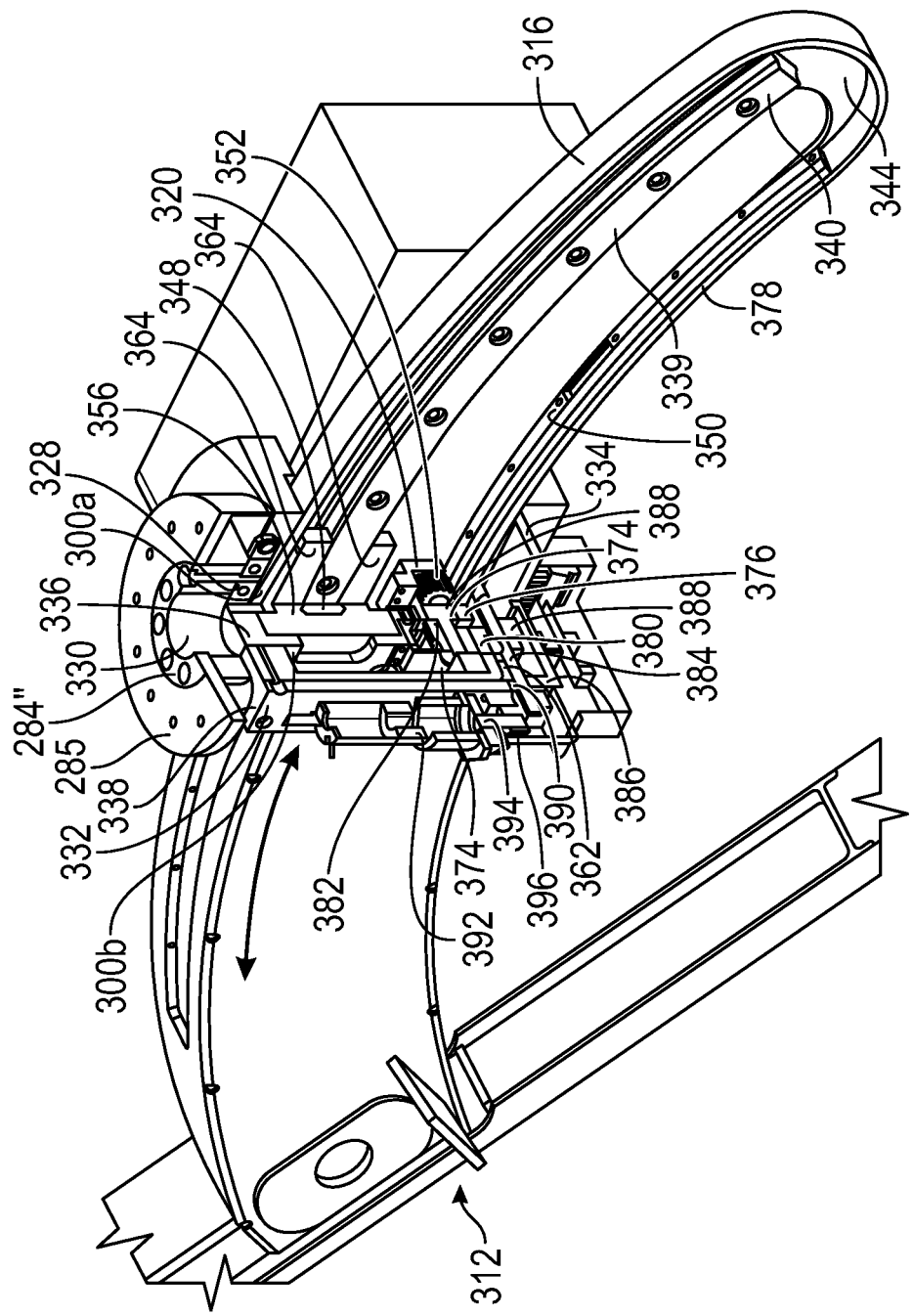
FIG. 10 is an isometric view, partially in section, of the arcuate slide of FIG. 9.

Arcuate driven slide 52 is suspended from the third planar translation member 40 by a flange 285 connected to the underside of the third planar translation member 40, such as by fasteners extending through the base of the third planar translation member and then into threaded apertures in the flange, or by other mechanisms. The third drive shaft 284" extends through the flange 285, and an arcuate drive housing 296 of the arcuate driven slide 52 is fixed to third drive shaft 284" at a location below the flange 285 such as by a spline and key arrangement, a threaded connection, a flange, or other connection mechanisms known in the art (not shown) such that arcuate drive housing 296 rotates about centerline or axis CL4, centerline or axis CL4 extends through the center 62 of the circumference of the arc along which driven arcuate member 52 extends. The arcuate driven slide 52 includes the arcuate drive housing 296 connected to the third drive shaft 284", and a driven arcuate slide member 298 which extends through a pair of slide apertures, first and second slide apertures 300a, b (in FIG. 10) respectively, extending through the arcuate drive housing 296 in the horizontal direction. In FIG. 9, the arcuate driven slide 52 of FIG. 1 is shown with the covering removed, to show the internal details thereof.

Arcuate slide member 298 here comprises an arcuate frame having upper and lower arcuate wall segments 302, 304, each lying on a portion of circles of different circumferences extending around the center 62, connected at the first end 306 thereof to a cap 308 having a curved, in plan view, contour, and at the opposed, second end 312 thereof, to a flat wall 314, the outer surface of which extends along a ray intersecting the center 62. Rotational motion of the third drive shaft 284" about its axis causes rotational movement of the arcuate drive housing 296, which in turn sweeps the flat wall 314 along an arc or circumferential path centered at the axis of rotation of the drive shaft 284". As the instrument controller 14 is connected directly to the flat wall 314, this motion likewise swings the body of the instrument controller along an arc or circumferential path centered at the centerline or axis CL4 of rotation of the drive shaft 284".

Upper and lower arcuate wall segments 302, 304 each further form a guide slot, upper guide slot 324 and lower guide slot 326 therein, bifurcating each of upper and lower arcuate wall segments 302, 304 into side by side wall portions, specifically first upper arcuate wall segment 316 and first lower arcuate wall segment 318 which extend through first slide aperture 300a, and second upper arcuate wall segment 320 and second lower arcuate wall segment 322 which extend through second slide aperture 300b. Cap 308, and flat wall 314 hold the upper and lower wall segments 316, 318, 320 and 322 in place at their opposed ends, and the configuration of the first and second slide apertures 300a, b maintain the same guide slot 324, 326 width as that at their opposed ends.

To form the guide slots 300a, 300b, arcuate slide member 298 includes a base plate 328, a middle segment 330 and opposed outer plates 332 (only one shown), spaced to either side of middle segment 330 connected together at their lower ends through a floor plate 334, and at their upper ends by a spacer 336 extending from the upper end of base plate 328, and a standoff 338 integrally formed at the upper end of the outer plate and secured to the spacer 336, such as by threaded fasteners and holes and corresponding threaded holes. Arcuate slide member 298 further includes a guide spline 339 supported, at its first guide spline end 340 by connection to a gusset 344 and at its second guide spline end 342, disposed on the opposite side of the first and second slide apertures 300a, b from the first end 340 to a second gusset 346, or the sidewall, of the arcuate slide member 298, such that the relative position of the side of the first guide slot 324 to the side of the guide spline is maintained constant over the length of the guide spline 339 A rack 350, in other words, a linear gear track, extends parallel to and alongside the second guide slot 326.

Middle segment 330 is configured to bifurcate the space between the opposed outer plates 332, and together with the base plate 328 and floor plate, form the pair of side by side first and second slide apertures 300a, b through which the upper and lower arcuate wall segments 302, 304 pass through the arcuate slide member 298. Additionally, a guide slot 348 extends through the middle segment 330, through which the guide spline 329 extends to support and guide the guide spline 328 therethrough, and position the gear teeth of a pinion 352 over, and into engagement with, the gear teeth of the rack 350. Thus, middle segment 330 includes the spacer 336, a spline guide plate 356 having the guide slot 348 therethrough positioned in a recess 360 of the spacer and a gearbox assembly 362. Spline guide plate 356 includes a guide member 364 composed of a plate 366 extending from a sidewall thereof, the spline guide slot having an arcuate extent therethrough and facing the surface of the base plate 328 to form an arcuate through opening.

Gearbox assembly 362 includes a first gear plate 374 having a through opening in which a first bearing 376 is secured, a second gear plate 378 connected to a side wall of the spacer 336 having a through opening in which a second bearing (not shown) is secured, and a second driven shaft 382 supported in the opposed bearings which supports a second idler gear 380 and on the distal end of which pinion 352 is secured. A first driven shaft 384 is disposed generally parallel to, and below second driven shaft 382, and is supported in a first driven shaft bearing 386 in an opening in the outer plate 332, and a second driven shaft bearing secured in an opening in the base plate 328 (opening and second bearing not shown). A first idler gear 388 is supported on first driven shaft 384, and the gear teeth thereof mesh with the teeth of the second idler gear 380. First driven shaft 384 extends through the opening securing and supporting first driven shaft bearing 386 therein, over which a second bevel gear 390 is secured.

Figure 11:
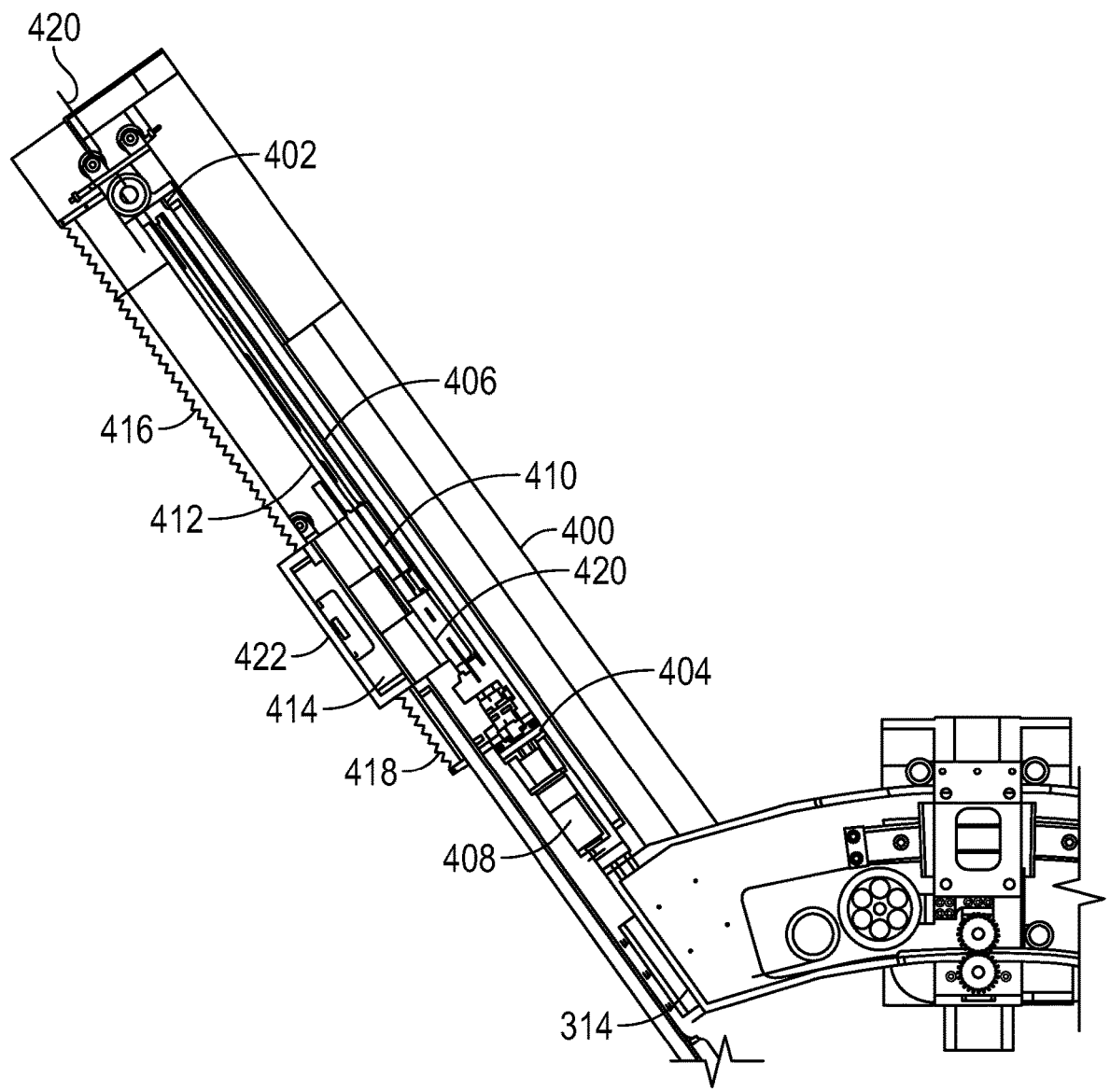
FIG. 11 is a plan view of a linear slide connected to the arcuate slide and configured to linearly position the instrument controller.

A bevel gear motor 392 is provided on the exterior of outer plate 332, and includes an output shaft 394 coupled to a first bevel gear 396, the teeth of which mesh with the teeth of second bevel gear 390. Rotation of the output shaft 394 by bevel gear motor 392 inducer rotation of first driven shaft 384 in a first direction (clockwise or counterclockwise) through the meshing of the first and second bevel gears 396, 390, which induces rotation of the second idler gear in the opposed direction through the coupling of first and second idler gears 388, 380, which causes the pinion 352 to rotate and thereby move the arcuate slide member 298 through the arcuate drive member 296, thereby moving the flat wall 314 to move along an arcuate path As shown in FIGS. 1 and 11, linear slide 48 is configured to move the instrument controller 14 in a straight line path, and here includes a linear slide housing 400 connected to and extending, in a cantilevered fashion from, the flat wall 314 of the arcuate slide member 298, within which are secured a opposed linear opposed guide stanchions 402, 404, within which opposed linear guide support bearings (not shown are supported, and into which a linear guide, here a linear guide threaded rod 406, is secured. A linear drive motor 408 is connected to the end of the linear guide threaded rod 406 extending past the stanchion 404, to selectively rotate the linear guide threaded rod 406 at a desired rotation velocity and direction. A guide block 410 having a finger (not shown) extending inwardly a groove 412 on the inner surface of the linear slide housing 400 is provided, and includes a through threaded opening (not shown) through which the linear guide threaded rod 406 threadingly extends. A reciprocating body 414 is connected, such as by threaded fasteners and corresponding holes and threaded holes, to the guide block 410. A first accordion pleated cover 416 extends over the opening in the linear slide housing 400 on a first side of the guide block 410, and a second accordion pleated cover 418 extends over the opening in the linear slide housing 400 on a second side of the guide block 410. The linear guide threaded rod 406 includes a linear guide threaded rod centerline 420 about which it rotates, and the mounting surface 422 of the guide block 410 to which the reciprocating body 414 is connected is parallel to the linear guide threaded rod centerline 420, which in turn is parallel to the end wall 314 of the arcuate slide member 298. The reciprocating body 414 includes an instrument controller mounting surface 422, which is parallel to the mounting surface 422 of the guide block 410 and thus parallel to the end wall 314 of the arcuate slide member 298. Rotation of the linear drive motor 408 causes the guide block 410, prevented from rotating by the finger extending into the groove 412, is induced to move linearly in the direction of the linear guide threaded rod centerline 420.

Referring back to FIG. 1, instrument controller 14 includes a drive portion 430, configured to rotate and linearly move, an insertion tube 432 extending therefrom, and a tube guide 434, including a tube guide opening therethrough (not shown) having a center on the centerline 436 of the instrument controller 14. The instrument controller 14 is mounted to the instrument controller mounting surface 422, such that the instrument controller mounting surface 422 and the centerline 436 of the instrument controller 14 are parallel to one another, and, the centerline 436 of the instrument controller 14 extends through, or essentially through, the center 62 of the circumference of the driven arcuate member 52, which is a reference location where an incision in a patient for entry of the insertion tube 432 thereinto.

To deploy the instrument controller 14 at a desired physical location and attitude relative to a patient, a technician, operator or surgeon wheels the instrument cart 10, using drive handles 70, 72, to a location such that the instrument controller is located adjacent to the patient. Then, using the touch screen on the control housing, the operator, technician or surgeon manipulates the planar translation members 32, 36 and 40, and the arcuate driven slide 52 such that the centerline 436 of the instrument controller 14 extends through the incision location in a patient for which the system is to be used to perform a surgical procedure, and the attitude (tilt with respect to the horizontal floor 84) is set to a desired state.

As described herein, instrument cart 10 is configured to position the tube guide 434 of the instrument controller 14 and the adjacent portion of a tubular device extending therethrough with seven degrees of freedom, including the elevation position of the lift portion 98 (first degree of freedom), the location of the first, second, and third drive shafts 284, 284' and 284" with respect to the center of the lift portion 98 (second, third and fourth degrees of freedom), the rotational orientation of the arcuate slide member 298 with respect to the third planar translation member 40 (fifth degree of freedom), the attitude, yaw or pitch of the linear slide 48 with respect to the floor 84, and the position of the instrument controller 14 with respect to the linear slide 48. Additionally, once the elevation and location of the center 62 of the circumference of the arc along which driven arcuate member 52 extends is positioned for introduction of a catheter or other tubular introduction device into a patient, only the arcuate drive housing 296, the arcuate driven slide 52 and the linear slide 48 need be operated to change the pitch, yaw or orientation of the tube guide 434, which operation will not cause the tube guide to be moved out of alignment with, or change the alignment orientation of the tube guide 434 with respect to, the center 62, while the instrument controller 14 operates to change the orientation of the distal end of the tubular introduction device being fed into a patient, all without causing the tube guide 434 to tear the patients skin and body wall.

The invention claimed is:

1. An instrument cart configured to position an instrument controller at a desired location and attitude pitch with respect to an incision location of a patient, comprising:
   a base;
   a lift member moveable with respect to the base;
   a first planar translation member connected to the lift member and arcuately moveable with respect thereto;
   a second planar translation member connected to the first planar translation member and arcuately moveable with respect thereto;
   a third planar translation member connected to the second planar translation member and arcuately moveable with respect thereto;
   an arcuate slide base connected to the third planar translation member and moveable with respect thereto; and
   an arcuate slide coupled to the arcuate slide base, and moveable with respect thereto; and an instrument controller coupling connected to the arcuate slide member, the instrument controller connected thereto and movable with respect thereto
   wherein the arcuate slide base comprises a guide slot
   wherein the arcuate slide further comprises an arcuate rack having rack gear teeth thereon; and
   the arcuate slide base further comprises a pinion having pinion gear teeth engageable with the rack gear teeth.

2. The instrument cart of claim 1, wherein the first, second and third planar translation members are each arcuately coupled at a first, second and third pivot location respectively, to allow distal ends thereof to each pivot location to swing or rotate thereabout, and the arcuate slide base is rotatably coupled to, and suspended from, the third planar translation member at a distal end of the third pivot location and wherein, the arcuate slide further comprises a linear slide coupled to the arcuate slide base, to which the instrument controller is connected for relative movement therebetween.

3. The instrument cart of claim 2, wherein the linear slide defines a centerline which is positioned perpendicular to a tangent of a circumference along which the arcuate slide extends, and the linear slide extends away from the arcuate slide in a direction away from a center of the circumference along which the arcuate slide extends, which, when the instrument controller is positioned, overlies, or is immediately adjacent to, the incision location of the patient.

4. The instrument cart of claim 3, wherein the instrument controller further defines a centerline which extends through the center of the circumference of the arcuate slide, whereby the instrument controller is moveable with respect to the linear slide along the centerline.

5. The instrument cart of claim 1, further comprising a gravity compensation mechanism disposed between the lifting member and the base, comprising:
   at least a freely rotatable pulley disposed at an upper end of the lifting member,
   a plurality of springs disposed at a lower end of the lifting member;
   at least a cable passing over the pulley and having a free end; and
   a compensation strap connected to the free end of the cable and a plurality of springs, wherein a downward force on the compensation strap supplied by the springs as the cable extends counterbalances the weight or mass of the lift member, and components connected thereto.

6. The instrument cart of claim 1, wherein the first planar member, the second planar member and the third planar member respectively comprises:
   a motor;
   a drive shaft extending from a central axis of each pivot location;
   a pulley being disposed coaxially around the drive shaft and having a belt connected over the pulley and to the motor; and
   a harmonic drive being connected between the driven shaft and the pulley, whereby the planar translation member swing about the central axis of the pulley when the motor rotates to drive the movement of the belt.

7. The instrument cart of claim 1, wherein the arcuate slide base further comprises a motor coupled to the pinion.

8. The instrument cart of claim 7, wherein the arcuate slide extends through the guide slot and is selectively positionable with respect to the arcuate slide base.

9. The instrument cart of claim 2, wherein the linear slide further comprises:
   a slide base;
   a motor,
   and a threaded rod coupled to the motor; and
   a guide block including a through threaded opening through which the threaded rod extends.

* * * * *